United States Patent [19]

Bechor et al.

[11] Patent Number: 5,076,275
[45] Date of Patent: Dec. 31, 1991

[54] VIEWING SYSTEM INERT TO MAGNETIC FLUX

[76] Inventors: Ronen Bechor, 4408 Golf Club L.N.; David Bekhor, 4804 Country Hills Dr., both of Tampa, Fla. 33624

[21] Appl. No.: 638,308

[22] Filed: Jan. 4, 1991

[51] Int. Cl.⁵ .................................................. A61B 5/55
[52] U.S. Cl. .................................. 128/653.2; 324/318; 381/90; 381/154
[58] Field of Search ................. 128/653 A, 653 SC; 324/318, 322; 381/94, 88, 90, 154, 159

[56] References Cited

U.S. PATENT DOCUMENTS

| | | | |
|---|---|---|---|
| 4,804,261 | 2/1989 | Kirschen | 351/158 |
| 4,901,141 | 2/1990 | Costello | 128/653 A |
| 4,903,703 | 2/1990 | Igarashi et al. | 128/653 A |
| 4,981,137 | 1/1991 | Kondo et al. | 128/653 A |

*Primary Examiner*—Ruth S. Smith
*Attorney, Agent, or Firm*—Joseph C. Mason, Jr.; Ronald E. Smith

[57] ABSTRACT

A viewing system for entertaining patients confined within a magnetic imaging device for prolonged periods of time. A remote source of moving video images feeds its output to a liquid crystal display projector that is positioned in close physical proximity to and within the magnetic field of the imaging device. The projector projects the moving video images onto a wooden screen that is also positioned in close physical proximity to and within the magnetic field of the imaging device. The screen is in substantial axial alignment with the longitudinal axis of the imaging device. The patient within the tube may wear spectacles that bend the light emanating from the projection screen into the patient's eyes so that the moving image on the screen can be viewed by a patient lying on his or her back and gazing upwardly at right angles to the projection screen. Alternatively, a non-metallic mirror member may be positioned within the tube so that the patient need not wear the special spectacles. Audio signals are delivered to the patient through air hoses connected to a headphone. The air hoses are fed audio signals by associated conical shaped members that are positioned within associated tubes, each of which has a first end that is closed by conventional speakers that are driven by selected sources of audio signals.

7 Claims, 2 Drawing Sheets

VIEWING SYSTEM INERT TO MAGNETIC FLUX

TECHNICAL FIELD

This invention relates, generally, to means for mentally occupying a patient who must remain calm and stationary within a magnetic resonance imager for extended periods of time.

BACKGROUND ART

Concern for individuals confined within magnetic resonance imaging devices for periods of about one hour has motivated several inventors to provide entertainment means to the patient during the confinement to ease the patient's anxiety and to make the time within the device seem to be relatively brief.

An apparently obvious solution to the problem would be simply to insert a television set, a radio, or other means for entertaining the patient, into a tube-like compartment occupied by the patient so that the patient may be entertained during the imaging process. That solution cannot work, however, because the magnetic flux density within the tube distorts video and audio signals and the source of video and audio signals also adversely affects the imaging apparatus, i.e., the T.V. set or radio and the imaging apparatus will interact and destroy the effectiveness of both.

One inventor, recognizing this limitation, positions a television set remote from the imaging device and extends optical fibers from the remote television set to a position within the imaging apparatus so that the patient is entertained. The optical fibers must be built into the imaging machine as original equipment, because it is believed that any attempt to retrofit such a system into an existing imaging device would be cost prohibitive. It is unknown whether such device actually works and if it does, how well it works. This system is disclosed in U.S. Pat. No. 4,901,141 to Costello.

The inventor of the optical fiber system points out that others have invented spectacles that enable the patient to view a fixed scene such as a still life that is positioned external to the tube, but that such systems have not been commercially successful because the prolonged viewing of a still life scene does not adequately entertain the patient for an extended period of time. Moreover, the problem cannot be solved by substituting a T.V. set for the fixed scene because the operation of the television set positioned within viewing range of the imaging apparatus will be disrupted by the magnetic flux of the imaging apparatus and vice versa.

Still another system for entertaining the patient includes a Liquid Crystal Display (LCD) video display system mounted within the tube where the patient can view it directly. However, LCD screens are relatively small and the patient remains incandescently aware of his or her confinement within the tube.

The prior art, considered as a whole in accordance with the requirements of law, neither teaches nor suggests how the limitations of the art could be overcome.

DISCLOSURE OF INVENTION

Commercially available spectacles that enable a recumbent individual to see objects placed in axial alignment with the individual's body in spaced relation to the individual's head are worn by a patient positioned within an imaging apparatus. Alternatively, a non-magnetic mirror means is positioned in the tube at a forty-five degree angle or other suitable angle above the eyes of the recumbent individual to accomplish the same effect.

A moving video image is then projected onto a suitable screen external to the imaging tube but in close physical proximity thereto so that the moving image may be viewed by the patient throughout the imaging process.

Sound is delivered to the patient through a unique conical device that delivers sound from speakers to a headphone worn by the patient within the tube.

The moving video image is supplied by a television set or video cassette recorder (VCR) or other suitable device that is positioned remote from the imaging apparatus. The remote positioning of the source of video and audio signals insures that said source is unaffected by the magnetic flux emanated by the imaging apparatus and vice versa.

Alternatively, audio signals are generated by conventional audio equipment such as an AM/FM radio, a compact disc (CD) player, a tape player, and the like. Controls are provided so that the individual within the tube may select among the audio signals available, or may select video and audio signals.

Accordingly, the moving video image is not transferred into the imagining tube, but remains on the projection screen external thereto.

Thus, it is understood that the primary object of this invention is to provide entertainment means for patients confined within imaging tubes wherein video and audio signals are selectively transmitted to the individual but where the source of said signals remains external to the imaging tube.

Another object is to disclose for the first time, anywhere in the world, a unique means for delivering audio signals to a patient in an imaging tube.

These and other important objects, advantages, and features of the invention will become apparent as this description proceeds. The invention accordingly comprises the features of construction, combination of elements and arrangement of parts that will be exemplified in the construction set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

BEST MODES FOR CARRYING OUT THE INVENTION

Figure 1:
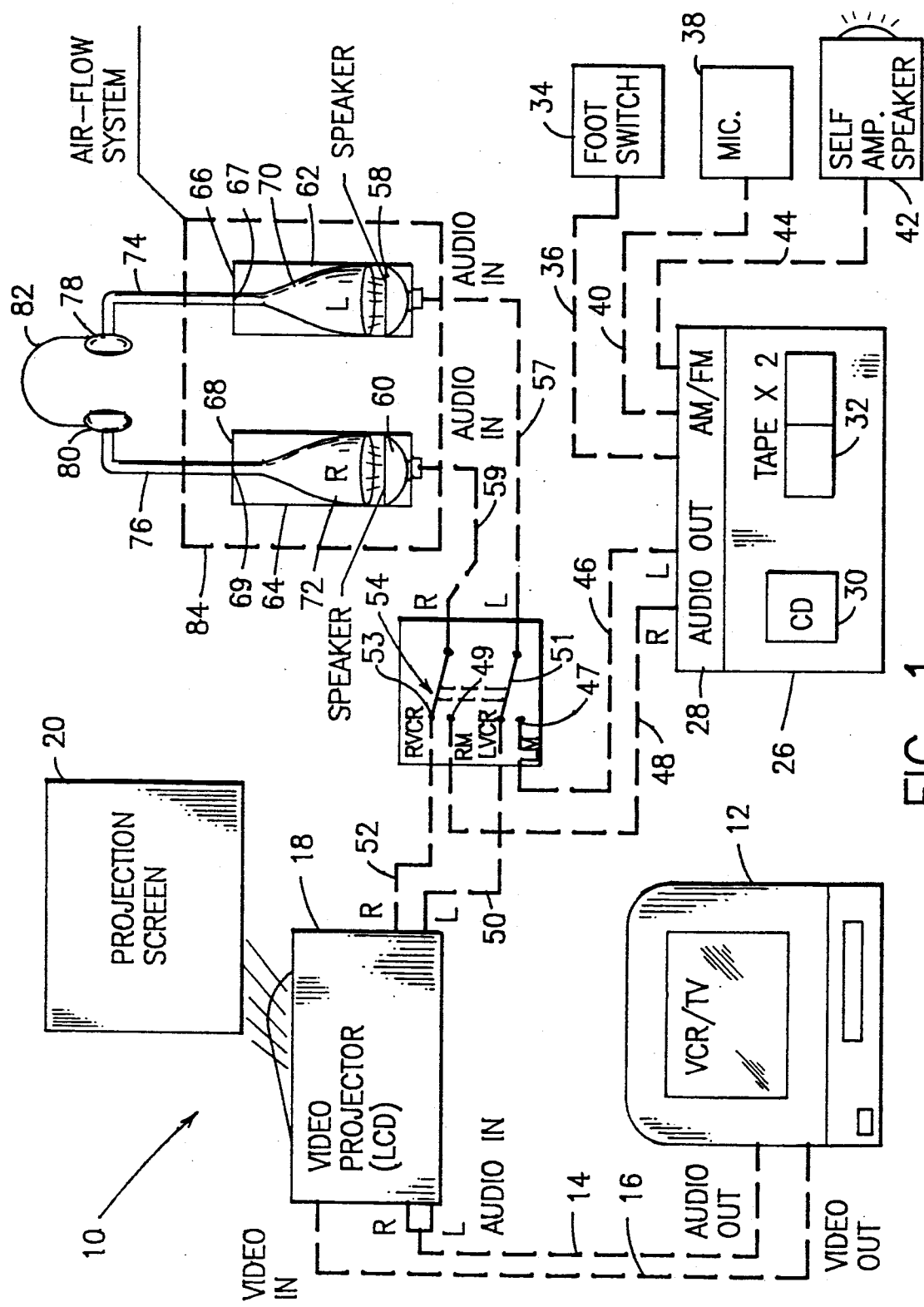
FIG. 1 is a diagrammatic view of the novel system.
Figure 1A:
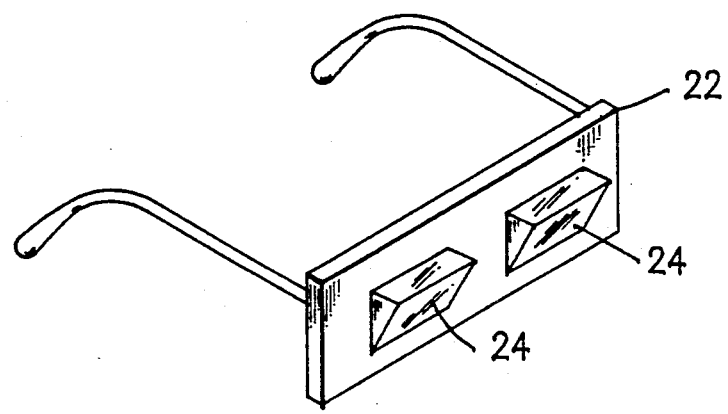
FIG. 1A is a perspective view of the spectacles that may be used as a part of the novel system.

Referring now to FIG. 1, it will there be seen that an exemplary embodiment of the present invention is denoted as a whole by the reference numeral 10.

A remote source of audio and video signals, such as a television set or a VCR is denoted 12 in FIG. 1; said source 12 is sufficiently far removed from the imaging device 11 (FIG. 2) as to have no magnetic interaction therewith. As shown in FIG. 1, these audio and video signals are fed over audio out and video out lines 14 and 16, respectively, to a video projector 18. The video projector has a liquid crystal display and such LCD is unaffected by the magnetic field of the imaging device. Accordingly, LCD projector 18, unlike the television set or VCR 12, is not positioned remote from the imaging device, as shown in FIG. 2, i.e., projector 18 is positioned within the magnetic field of device 11.

Figure 2:
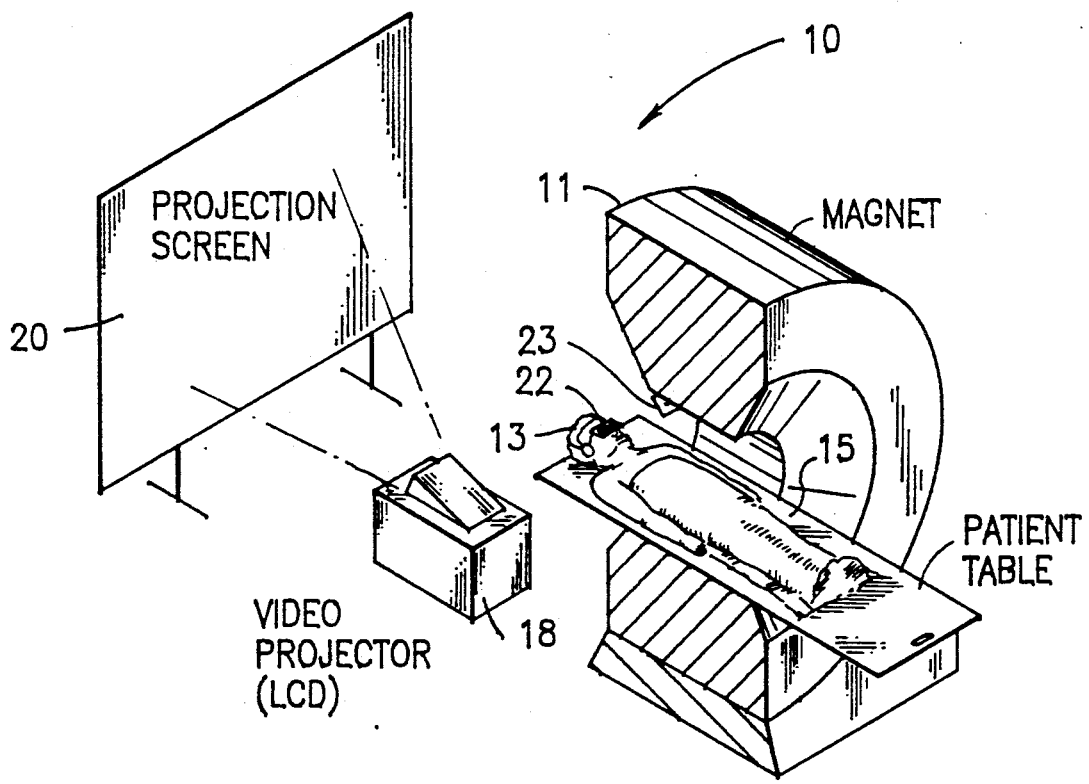
FIG. 2 is a diagrammatic view showing how the projection screen is in substantial axial alignment with the imaging tube.

A wooden and thus non-magnetic projection screen 20 is positioned adjacent projector 18 and it is this screen 20 that is viewed by the patient 13 lying in the imaging device 11 on patient table 15 (FIG. 2). Thus, it should be understood that screen 20 is positioned in substantial axial alignment with the tube of the imaging device, rearwardly of the patient's head and in reasonably close physical proximity to the patient's head, as shown in FIG. 2.

Special glasses 22 are worn by the patient when in the tube 11, in the first embodiment of this invention. The spectacles include a pair of prisms 24 that are mounted on a rotatable base plate; non-magnetic materials are used in the construction of said spectacles. No detailed description of the spectacles is needed because the spectacles are commercially available from Cleo, Inc. of Cleveland, Ohio, and are patented in a country foreign to the U.S. The prisms enable a recumbent patient to gaze directly straight ahead and to see the screen 20; thus, it should be understood that photons of light from the screen 20 travel, at least in part, parallel to the longitudinal axis of the imaging device and enter the tube occupied by the patient. The prisms capture some of those photons and reflect them ninety degrees downwardly into the patient's eyes, thereby enabling the patient to see the entire screen 20 in detail.

The moving video image on screen 20 thus remains on said screen, i.e., it remains external to the imaging tube and is never transferred into the tube nor does it cross a magnetic gradient as in the Costello system mentioned earlier that employs optical fibers to transfer the image across the gradient and into the tube for viewing by the patient.

Moreover, the patient is not restricted to viewing a still life painting.

Moreover, spectacles 22 are not critical to this invention. A simple, adjustable reflective means 23 (FIG. 2) could be mounted within the imaging tube in the patient's line of sight, above the recumbent patient's head. Numerous light reflecting, mirror-like materials are commercially available that are non-magnetic, such as the material used in the spectacles available from Cleo, Inc.

The balance of this disclosure relates to means for bringing audio signals from source 12, or some other source of audio signals to the patient within the tube. Electronic devices such as AM/FM radios, tape and CD players, like television sets and VCR's, are magnetically interactive with the imaging tube, and cannot be placed in close physical proximity thereto.

The novel system, in addition to video and audio source 12, also provides audio source 26 which may include an AM/FM radio 28, a CD player 30, a single or dual cassette tape player 32, or other suitable source of audio signals.

A foot switch or other suitable switch means 34 is conductively coupled to audio source 26 by line 36 and enables a technician to mute the audio output of audio source 26 so that a technician or physician may speak to patient 13 over microphone 38. Microphone 38 is conductively coupled to audio source 26 over line 40. A self-amplifying speaker 42, connected to audio source 26 by line 44, provides the audio gain that may be needed and is of course adjustable to the comfort of the patient.

Source 26 has left and right audio out lines 46, 48, and video projector 18 has left and right audio out lines 50, 52. The left audio out lines 46 and 50 terminate at terminals 47 and 51, respectively, and the right audio out lines 48 and 52 terminate at terminals 49 and 53, respectively. A double pole, double throw switch 54 is thrown by an operator to select audio from either projector 18 or audio source 26; in FIG. 1, switch 54 is thrown to feed audio signals from projector 18. The selected audio source feeds its signal to a left speaker 58 and a right speaker 60 over lines 57 and 59, respectively, as shown in FIG. 1.

Importantly, each speaker 58, 60 is mounted in closing relation to an associated closed end tube 62, 64, respectively, said tubes being closed at a first end by said speakers and closed at a second end by walls 66, 68, respectively.

A conical member 70, 72 is positioned concentrically within its associated tube 62, 64 as shown; accordingly, sound emanated by speakers 58, 60 is constrained to enter conical members 70, 72 as should be apparent from FIG. 1. The funnel-like contour of the conical members feeds the audio signal to associated air tubes 74, 76 which are physically connected to earphones 78, 80 which are interconnected by flexible band 82. Note that end walls 66 and 68 are apertured as at 67, 69, respectively, and that air tubes 74, 76 are confluent with said apertures. Conical members 70, 72 are also confluent with said apertures so that sound from said speakers is fed to said earphones without obstruction. The patient may be provided with controls that enable him or her to control the audio gain of the earphones, also known as headphones, or to select the source of audio and video signals.

Speakers 58, 60 and the conical members 70, 72 are physically within the air flow system of the imaging device, as denoted by box 84.

This invention is clearly new and useful. Moreover, it was not obvious to those of ordinary skill in this art at the time it was made, in view of the prior, considered as a whole.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A viewing system for a patient disposed in a recumbent position within a magnetic resonance imaging device having a magnetic field, comprising:

a magnetically inert projection screen;

said magnetically inert projection screen positioned external to said magnetic resonance imaging device but within the magnetic field of said device;

said magnetically inert projection screen being positioned in substantial axial alignment with a longitudinal axis of said device;

image reflecting means inert to said magnetic field positioned within said device; and magnetically inert projector means positioned external to said magnetic resonance imaging device but within said magnetic field for projecting a moving video image onto said magnetically inert projection screen;

said image reflecting means adapted to reflect light from said moving video image into the eyes of said patient.

2. The system of claim 1, further comprising means inert to said magnetic field for introducing audio signals from a source of audio signals external to said device into said device.

3. The system of claim 2, wherein said means for introducing audio signals into said device includes at least one earphone means adapted to abuttingly engage an ear of said patient within said tube, at least one speaker member in electrical communication with a preselected source of audio signals, at least one tube having a closed end and an open end, said at least one speaker being positioned at said open end of said at least one tube to close said open end, a conical member concentrically positioned within said tube, an aperture formed in the closed end of said tube, said conical member being confluent with said aperture, and an air tube disposed in interconnecting relation between said at least one earphone and said aperture so that sound emanating from said speaker is transmitted through said air tube to said at least one earphone.

4. The system of claim 1, wherein said magnetically inert projector means is a liquid crystal display video projector.

5. The system of claim 1, further comprising source means for delivering audio and video signals to said projector means, said source means being positioned remote from the magnetic field of said magnetic resonance imaging device.

6. The system of claim 5, wherein said source means is a television set.

7. The system of claim 5, wherein said source means is a video cassette recorder.

* * * * *